United States Patent
Takahashi et al.

(10) Patent No.: US 9,454,804 B2
(45) Date of Patent: Sep. 27, 2016

(54) IMAGE PROCESSING DEVICE AND IMAGE PROCESSING METHOD

(71) Applicant: HITACHI MEDICAL CORPORATION, Tokyo (JP)

(72) Inventors: Hisashi Takahashi, Tokyo (JP); Koichi Hirokawa, Tokyo (JP); Taiga Goto, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 40 days.

(21) Appl. No.: 14/372,330

(22) PCT Filed: Mar. 14, 2013

(86) PCT No.: PCT/JP2013/057118
§ 371 (c)(1),
(2) Date: Jul. 15, 2014

(87) PCT Pub. No.: WO2013/146283
PCT Pub. Date: Mar. 10, 2013

(65) Prior Publication Data
US 2015/0010224 A1    Jan. 8, 2015

(51) Int. Cl.
G06T 5/00    (2006.01)
G06T 5/50    (2006.01)
G06T 11/00   (2006.01)
A61B 6/03    (2006.01)
A61B 6/00    (2006.01)

(52) U.S. Cl.
CPC .............. *G06T 5/002* (2013.01); *A61B 6/032* (2013.01); *A61B 6/5205* (2013.01); *G06T 5/005* (2013.01); *G06T 5/50* (2013.01); *G06T 11/008* (2013.01); *G06T 2207/10081* (2013.01); *G06T 2207/20224* (2013.01); *G06T 2207/30004* (2013.01); *G06T 2211/40* (2013.01)

(58) Field of Classification Search
None
See application file for complete search history.

(56) References Cited

U.S. PATENT DOCUMENTS 5,991,457 A  * 11/1999  Ito et al. ................. 382/254
6,381,298 B2    4/2002  Proksa et al.
(Continued)

FOREIGN PATENT DOCUMENTS

CN    1521695 A    8/2004
JP    2001-198120   7/2001
(Continued)

OTHER PUBLICATIONS

International Search Report in PCT/JP2013/057118.
(Continued)

*Primary Examiner* — Michelle Entezari
(74) *Attorney, Agent, or Firm* — Coope & Dunham LLP

(57) ABSTRACT

In order to provide an image processing device and the like making it possible to generate a target image in which edges of a structure are upheld and from which streaking artifacts are removed, a computation device determines a shape of a non-linear function on the basis of feature amounts of an original image and a smoothed image (S101). Next, the computation device calculates a condition coefficient of the original image and the smoothed image by using the non-linear function for which the shape was determined in S101 (S102). Next, the computation device uses the condition coefficients calculated in S102 to calculate a weighting coefficient for each of the pixels of the original image and the smoothed image (S103). Next, the computation device adds weighting to the original image and the smoothed image to generate the target image (S104).

14 Claims, 6 Drawing Sheets

41

42

(56) References Cited

U.S. PATENT DOCUMENTS

| | | | |
|---|---|---|---|
| 6,667,815 B1* | 12/2003 | Nagao | 358/1.9 |
| 2001/0014140 A1 | 8/2001 | Proksa et al. | |
| 2003/0235327 A1* | 12/2003 | Srinivasa | 382/104 |
| 2006/0215925 A1* | 9/2006 | Kuniba | G06T 7/0004 382/254 |
| 2006/0245002 A1* | 11/2006 | Kita | 358/3.26 |
| 2007/0145317 A9 | 6/2007 | Kobayashi et al. | |
| 2009/0147919 A1 | 6/2009 | Goto et al. | |
| 2009/0208129 A1* | 8/2009 | Shimodaira | G06T 5/002 382/264 |
| 2010/0195926 A1* | 8/2010 | Sasaki | 382/260 |
| 2011/0081096 A1* | 4/2011 | Kim | 382/264 |

FOREIGN PATENT DOCUMENTS

| | | |
|---|---|---|
| JP | 3700798 | 7/2005 |
| JP | 2007-44275 | 2/2007 |
| JP | 2010-226694 | 10/2010 |

OTHER PUBLICATIONS

J. Hsieh "Adaptive streak artifact reduction in computed tomography resulting from excessive x-ray photon noise", Med. Phys., vol. 25, No. 11, p. 2139-2147.

T. Li et al., "Nonlinear Sinogram Smoothinfor Low-Dose X-Ray CT", IEEE, Trans. Nuc l., vol. 51, No. 5, p. 2505-2513, 2004.

* cited by examiner

IMAGE PROCESSING DEVICE AND IMAGE PROCESSING METHOD

BACKGROUND OF THE INVENTION

1. Field of the Invention

The present invention relates to an image processing device that performs image processing on an image obtained by using an X-ray CT apparatus and so forth, and more particularly relates to a technology that maintains an original shape of the edge of a structure and removes streak artifacts.

2. Description of the Related Art

In an image reconstructing method, the X-ray CT apparatus reconstructs a tomographic image of a test object by irradiating the test object with X-rays from around the object and back-projecting real projection data acquired at a plurality of projection angles.

When an image of flat body part such as the shoulder and so forth of the test object is to be reconstructed on the basis of original information obtained by such an X-ray CT apparatus as aforementioned, in a case where an exposure dose of the X-rays is insufficient, the streak artifacts are generated in a direction which is large in X-ray attenuation. A technique of reducing the streak artifacts by smoothing projection data and thereafter applying the aforementioned image reconstructing method is proposed in J. Hsieh, "Adaptive streak artifact reduction in computed tomography resulting from excessive x-ray photon noise", Med. Phys. Vol. 25, No. 11, pp. 2139-2147, 1998 and T. Li et. al., "Nonlinear Sinogram Smoothing for Low-Dose X-ray CT", IEEE. Trans. Nucl. Sci., Vol. 51, No. 5, pp. 2505-2513, 2004. Hereinafter, a device for reducing these streak artifacts will be referred to as a "projection data smoothing filter".

In an image obtained by the projection data smoothing filter, an edge of a comparatively high-contrast structure is blurred in association with attainment of a streak artifact reducing effect. The streak artifact reducing effect and a structure edge maintaining effect are in a trade-off relation and the more the former effect is increased, the more the latter effect is decreased. Accordingly, in a case where strong streak artifacts are reduced, the edge of the structure may be greatly blurred. Since the blur on the edge of the structure is not favorable in clinical diagnosis, an image (hereinafter, referred to as a "target image") that the edge of the structure is maintained and the streak artifacts are removed is expected.

As a means of settling the above-mentioned disadvantage, a method of appropriately adding together with weighting an image (hereinafter, referred to as an "original image") obtained from the projection data by the aforementioned image reconstructing method and an image (hereinafter, referred to as a "smoothed image") obtained from projection data which has been smoothed by application of the projection data smoothing filter by the aforementioned image reconstructing method is given. That is, the aforementioned target image is obtained by performing weighted addition such that the percentage of a pixel value of the smoothed image is increased in pixels of a part that the streaked artifact is generated on the image and the percentage of a pixel value of the original image is increased in pixels of the edge part of the structure. Several techniques of mixing together two images which are generated from the same original information as mentioned above have been proposed so far.

In the technique described in Japanese Patent No. 3700798, a low-resolution image which is lower in resolution than the original image is created from the original image, the edge is detected from the low-resolution image and a low-resolution edge image is created, and a weighting coefficient is calculated from an edge luminance value of the low-resolution edge image using a nonlinear function. At that time, a difference between a maximum value and a minimum value of values of pixels in a predetermined region including a pixel of interest, and a variance value, a concentration gradient and so forth thereof are used in detection of the edge. The edge of the structure is enhanced by adding an image that the low-resolution image has been differentiated from the original image to the original image with weighting by using the aforementioned weighting coefficient. It is possible to perform weighted addition of the original image and the smoothed image by such a technique.

In the technique described in Japanese Patent Application Laid-Open No. Hei07-93543, an image is divided into small regions, a standard deviation value of the small regions is calculated, a histogram that the standard deviation value is used for classification targeting on all of the small regions is prepared, and a discrimination class value is calculated from the histogram to classify each small region into a flat region and a non-flat region. Detecting the edge of the structure on the image is equivalent to discriminating between the flat region and the non-flat region. If it is possible to classify each small region into both of the flat region and the non-flat region, it will become possible to perform weighted addition of the original image and the smoothed image by using the pixel value of the original image in the non-flat region and using the pixel value of the smoothed image in the flat region.

SUMMARY OF THE INVENTION

Incidentally, the strong streak artifact has a characteristic similar to that of a linear structure unlike granular noise generated in an image. Then, in a case where detection of the edge is performed by using the difference between the maximum value and the minimum value of the values of the pixels in the predetermined region including the pixel of interest, and the variance value, the concentration gradient and so forth thereof as in the technique described in Japanese Patent No. 3700798, the possibility that the strong streak artifact may be erroneously detected as the edge is high.

In addition, the strong streak artifact has the characteristic similar to that of the linear structure as mentioned above. Then, in a case where decision of the structure concerned is made on the basis of the standard deviation value as in the technique described in Japanese Patent Application Laid-Open No. Hei07-93543, it is feared that the region including the streak artifact may be erroneously recognized as the non-flat region.

In a case where the streak artifacts have been erroneously recognized as the structure and the edge of the structure, part or whole of each streak artifact may be restored in an image obtained after the original image and the smoothed image haven been subjected to weighted addition. That is, it is difficult to obtain the target image by the techniques described in Japanese Patent No. 3700798) and Japanese Patent Application Laid-Open No. Hei07-93543.

A fundamental reason why it is difficult to obtain the target image lies in the point that the techniques described in Japanese Patent No. 3700798 and Japanese Patent Application Laid-Open No. Hei07-93543 aim to classify the granular noise separately from the structure in a uniform region and do not use an index for classifying the streak artifact separately from the structure.

The present invention has been made in view of the above-mentioned disadvantages and it is desirable to provide an image processing device and an image processing method allowing generation of the target image that the edge of the structure is maintained and the streak artifact is removed.

According to an embodiment of a first invention, there is provided an image processing device that adds respective mutually corresponding pixels of an original image generated from original information and of a smoothed image generated from the same original information and reduced at least in streak artifact with weighting using a weighting coefficient and generates a target image that an edge of a structure is maintained and the streak artifact is removed, including a function shape determination unit that determines a shape of a nonlinear function on the basis of feature amounts of the aforementioned original image and the aforementioned smoothed image and a weighting coefficient calculation unit that calculates aforementioned weighing coefficient on the basis of the aforementioned nonlinear function.

According to an embodiment of a second invention, there is provided an image processing method that adds respective mutually corresponding pixels of an original image generated from original information and of a smoothed image generated from the same original information and reduced at least in streak artifact with weighting using a weighting coefficient and generates a target image that an edge of a structure is maintained and the streak artifact is removed, including the function shape determination step of determining a shape of a nonlinear function on the basis of feature amounts of the aforementioned original image and the aforementioned smoothed image and the weighting coefficient calculation step of calculating the aforementioned weighting coefficient on the basis of the aforementioned nonlinear function.

Advantageous Effect of the Invention

According to the embodiments of the present inventions, it is possible to provide the image processing device and the image processing method allowing generation of the target image that the edge of the structure is maintained and the streak artifact is removed.

DETAILED DESCRIPTION OF THE PREFERRED EMBODIMENTS

Embodiments of the present invention will be described in detail on the basis of the following drawings. First, a configuration of an X-ray CT apparatus 1 will be described with reference to FIG. 1 and FIG. 2.

Figure 1:
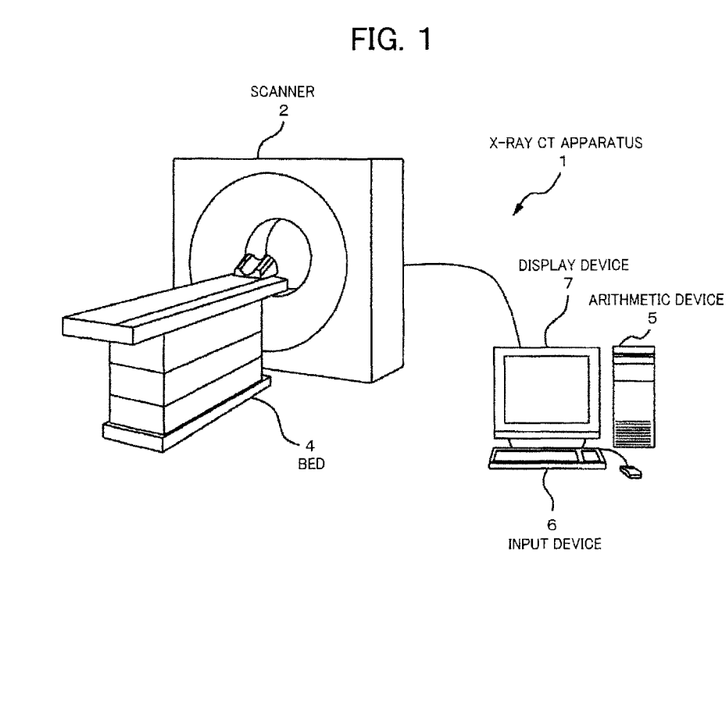
FIG. 1 is a general schematic diagram illustrating one example of an X-ray CT apparatus.

As illustrated in FIG. 1, the X-ray CT apparatus 1 includes a scanner 2 on which an X-ray tube 11 and a detector 12 are loaded, a bed 4 on which a test object 10 is placed, an arithmetic device 5 that processes data obtained from the detector 12, an input device 6 such as a mouse, a trackball, a keyboard, a touch panel and so forth, a display device 7 that displays a reconstructed image and so forth and others.

An operator inputs imaging conditions, reconstruction parameters and so forth via the input device 6. The imaging conditions are, for example, a bed feed rate, a tube current, a tube voltage, a slice position and so forth. In addition, the reconstruction parameters are, for example, a region of interest, a reconstructed image size, a back projection phase width, a reconstruction filter function and so forth.

Figure 2:
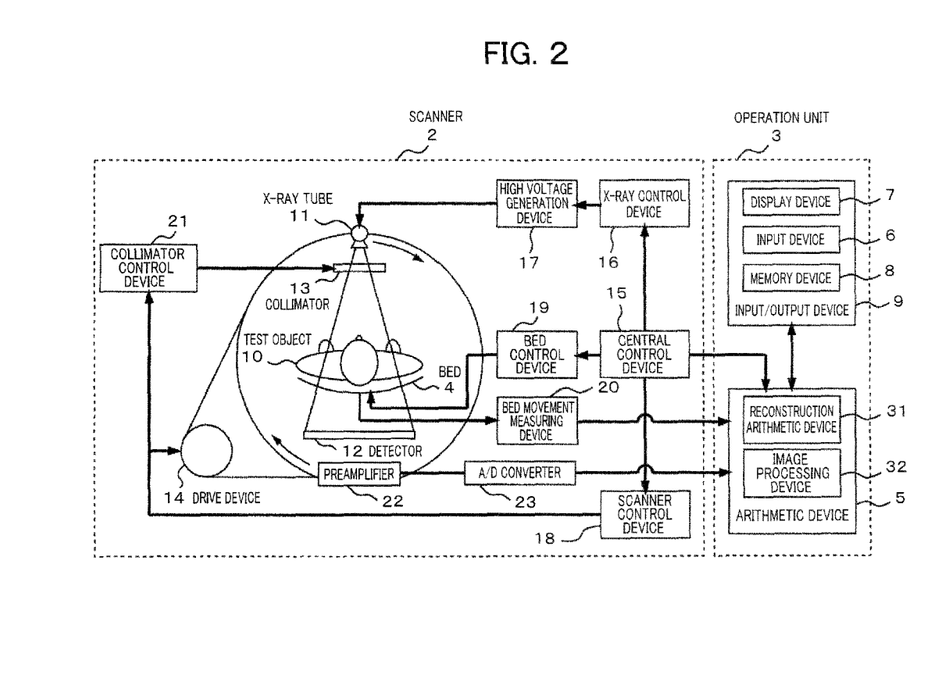
FIG. 2 is a diagram illustrating one general configuration example of the X-ray CT apparatus.

As illustrated in FIG. 2, the X-ray CT apparatus 1 includes the scanner 2, an operation unit 3 and the bed 4 when broadly classified. The scanner 2 includes the X-ray tube 11 (an X-ray source), the detector 12 (an X-ray detector), a collimator 13, a drive device 4, a central control device 15, an X-ray control device 16, a high-voltage generation device 17, a scanner control device 18, a bed control device 19, a bed movement measuring device 20, a collimator control device 21, a preamplifier 22, an A/D converter 23 and so forth.

The X-ray CT apparatus 1 is broadly classified into a multislice CT using the detector 12 that detection elements are arrayed in two-dimensional directions and a single slice CT using the detector 12 that the detection elements are arrayed in line, that is, in one-dimensional direction (only in a channel direction). In the multislice CT, X-ray beams which spread in a cone-like form or in a pyramid-like form are irradiated from the X-ray tube 11 which is an X-ray source conforming with the detector 12. In the single slice CT, the X-ray beams which spread in a fan-like form are irradiated from the X-ray tube 11. In general, in imaging using the X-ray CT apparatus 1, X-ray irradiation is performed while a gantry part is going around the test object 10 placed on the bed 4.

The central control device 15 controls to input the imaging conditions and the reconstruction parameters through the input device 6 in the operation unit 3 and to transmit control signals desired for imaging to the collimator control device 21, the X-ray control device 16, the scanner control device 18 and the bed control device 19. The collimator control device 21 controls the position of the collimator 13 on the basis of the control signal.

When imaging is started by receiving an imaging start signal, the X-ray control device 16 controls the high-voltage generation device 17 on the basis of the control signal. The high-voltage generation device 17 applies the tube voltage and the tube current to the X-ray tube 11. In the X-ray tube 11, electrons of energy according to the applied tube voltage are emitted from a cathode and the emitted electrons strike a target (an anode), thereby irradiating the test object 10 with the X-ray of energy according to the energy of the electrons.

In addition, the scanner control device 18 controls the drive device 14 on the basis of the control signal. The drive device 14 drives the gantry part on which the X-ray tube 11, the detector 12, the preamplifier 22 and so forth are loaded so as to go around the test object 10. The bed control device 19 controls the bed 4 on the basis of the control signal.

The X-ray irradiated from the X-ray tube 11 is controlled by the collimator 13 in irradiation region, is absorbed (attenuated) in accordance with an X-ray attenuation coefficient into each tissue in the test object 10, passes through the test object 10 and is detected by the detector 12 arranged at a position facing the X-ray tube 11. The detector 12 includes the plurality of detection elements which are arrayed in the two-dimensional directions (the channel direction and a column direction orthogonal to the channel direction. The X-ray received by each detection element is converted into real projection data.

That is, the X-ray detected by the detector 12 is converted into current, is amplified by the preamplifier 22, is converted into digital data by the A/D converter 23, is subjected to logarithmic transformation, is calibrated and is input into the arithmetic device 5 as the real projection data.

At that time, since the mutually facing X-ray tube 11 and detector 12 rotate around the test object 10, the real projection data is collected at discrete X-ray tube positions (and corresponding detector positions) in a rotation direction. A real projection data acquisition unit at each X-ray tube position is called a "view".

The arithmetic device 5 includes a reconstruction arithmetic device 31, an image processing device 32 and so forth. In addition, an input/output device 9 includes the input device 6, the display device 7, a memory device 8 (a memory unit) and so forth.

The reconstruction arithmetic device 31 performs an image reconstructing process using the real projection data and generates a reconstructed image. The reconstruction arithmetic device 31 generates filtered projection data by superimposing a reconstruction filter on the real projection data of each view and performs back projection processing on the filtered projection data by adding weight in a view direction, thereby non-destructively imaging a tomographic image as a distribution map of an x-ray attenuation coefficient in the test object 10.

The reconstruction arithmetic device 31 stores the generated reconstructed image into the memory device 8. In addition, the reconstruction arithmetic device 31 displays the reconstructed image as a CT image on the display device 7. Alternatively, the image processing device 32 may perform image processing on the reconstructed image stored in the memory device 8 and displays the image so processed as the CT image on the display device 7.

In the following, an image processing method that adds respective mutually corresponding pixels of an original image generated from original information acquired by the X-ray CT apparatus 1 and so forth and a smoothed image which is generated from the same original information and is reduced at least in streak artifact with weighting by using a weighting coefficient and generate a target image that the edge of the structure is maintained and the streak artifact is removed will be described.

In the image processing method according to the embodiment of the present invention, the target image is generated so as to meet the following three constraint conditions.

(Constraint Condition 1) The pixel value of the target image is to be within a range of pixel values of mutually corresponding pixels in the original image and the smoothed image.

(Constraint Condition 2) The target image is to be an image which is smooth spatially (that is, in one image space).

(Constraint Condition 3) The target image is to be suppressed in increase in noise such as the streak artifact and so forth in a region (=one of the flat regions) which is thought to be the same organ in comparison with the smoothed image.

The constraint condition 1 is a condition which has been defined in order not to lose the original image (however, the noise is excluded) acquired by the X-ray CT apparatus 1 and so forth. The constraint condition 1 may be expressed in such a different form as min (a minimum pixel value of the original image and a minimum pixel value of the smoothed image) ≤ a pixel value of the target image ≤ max (a maximum pixel value of the original image and a maximum pixel value of the smoothed image). Incidentally, min( ) is an operator for outputting a minimum value and max( ) is an operator for outputting a maximum value.

The constraint condition 2 is a condition which has been defined in order to avoid discontinuity which would occur in the target image. The constraint condition 3 is a condition which has been defined in order to remove mainly the granular noise and the streak artifact. The image processing method according to the embodiment of the present invention features to meet the constraint condition 3 in particular.

The weighting coefficient used for weighted addition is determined by condition coefficients indicating the conditions of the original image and the smoothed image. The condition coefficient has a value of a nonlinear function that a difference in pixel value between a pixel of interest of the original image or the smoothed image and an adjacent pixel thereof is set as a variable.

In the embodiment of the present invention, a generalized Gaussian function is used as the nonlinear function. However, any nonlinear function will do as long as it is a smooth continuous function, has a plurality of arbitrary parameters and is arbitrarily adjustable in shape, and there is no particular limit thereon. If the nonlinear function is the smooth continuous function, the aforementioned "(Constraint Condition 2) The target image is to be an image which is smooth spatially (that is, in one image space)" will be met. As other examples of the nonlinear function, a logistic function and so forth may be given.

An image vector is put as $x=(x_1, \ldots, x_J)$, a set of adjacent pixels r relative to a pixel of interest s is put as $N_s$ and a condition coefficient $g_s(x)$ of the pixel of interest s is defined by the following formula using the generalized Gaussian function.

[Numerical Formula 1]

$$g_s(x, v) \equiv \exp\left\{-\sum_{r \in N_s} \frac{w_{sr}|x_s - x_r|^p}{2v^p}\right\} \quad (1)$$

Here, p is an arbitrary parameter for adjusting the gradient of the generalized Gaussian function and is set to have the same value for all slices. v is an arbitrary parameter for adjusting a bending position of the generalized Gaussian function. $W_{sr}$ is a weighting coefficient according to a distance between the pixel of interest s and the adjacent pixel r and is defined, for example, as in the following formula.

[Numerical Formula 2]

$$w_{sr} = \exp\left(-\frac{l_{sr}^2}{2L^2}\right) \quad (2)$$

Here, $l_{sr}$ is the distance between the pixel of interest s and the adjacent pixel r. L is a ratio of the size of a pixel to the size of an element of the detector. However, $w_{sr}$ may not necessarily be limited to the formula (2) and may be a function whose value is increased as the adjacent pixel r is closer to the pixel of interest s. In addition, the set $N_s$ of pixels adjacent to the pixel of interest s and the gradient p of the generalized Gaussian function may be empirically determined.

Figure 3:
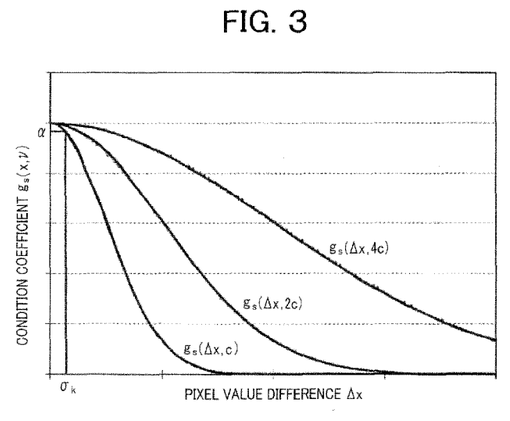
FIG. 3 is a diagram illustrating examples of function shapes of nonlinear functions.

In the formula (1), if the pixel values of the pixel of interest s and the adjacent pixel r are equal to each other, the condition coefficient will become 1, and the larger the difference in pixel value between the pixel of interest s and the adjacent pixel r is, the more the condition coefficient will approach 0. One example of a change in shape of functions when ν has been set to arbitrary constants c, 2c and 4c for the difference in pixel value between the pixel of interest s and the adjacent pixel r is illustrated in FIG. 3. Thinking of the situation by fixing the difference in pixel value, the more ν is increased, the more the condition coefficient is liable to have a value close to 1. According to the embodiment of the present invention, the parameter ν for adjusting the bending position of the function is determined such that the condition coefficient has a value almost close to 1 relative to the difference in pixel value between the pixel of interest s and the adjacent pixel r which would occur due to the presence of the streak artifact in one tomographic image.

[First Embodiment]

Figure 4:
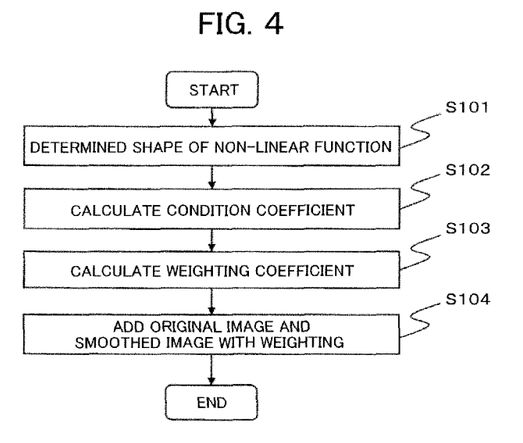
FIG. 4 is a diagram illustrating one example of a general processing flow.

In the following, the first embodiment of the present invention will be described following the stream of a processing flow illustrated in FIG. 4 while appropriately referring to other drawings.

<Step S101>

The arithmetic device 5 of the X-ray CT apparatus 1 (hereinafter, referred to as the "arithmetic device 5) determines the shape of the nonlinear function on the basis of feature amounts of the original image and the smoothed image. A process of determining the shape of the nonlinear function will be described later with reference to FIG. 5.

<Step S201>

Figure 6:
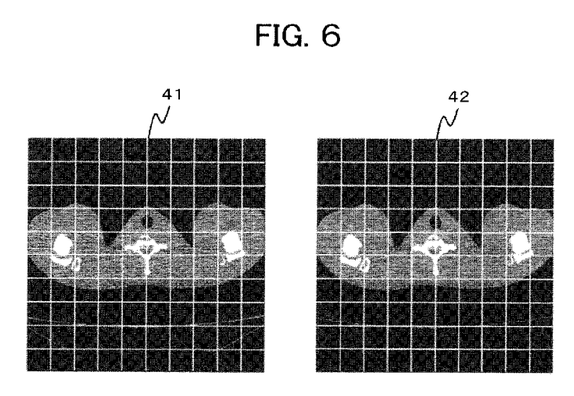
FIG. 6 is a diagram illustrating examples of region division of an original image and a smoothed image.

The arithmetic device 5 divides regions of the original image and the smoothed image into mutually corresponding small regions. For example, as illustrated in FIG. 6, the arithmetic device 5 partitions the regions of an original image 41 and a smoothed image 42 in a lattice shape and divides them into small regions. The size of the small region is empirically determined.

However, the method of dividing one region into small regions is not limited to this example. In the embodiment of the present invention, the regions of the original image 41 and the smoothed image 42 may be just divided into the small regions by the same dividing method. In addition, the shape of the small region is not limited to a rectangle. In the embodiment of the present invention, the plurality of adjacent pixels may be included in the same small region. In addition, one pixel may be included in the plurality of small regions redundantly.

<Steps S202, S203>

The arithmetic device 5 calculates variation values of the original image 421 and the smoothed image 42 from the pixel values of the pixels included in the small region for each of the respective small regions pertaining to both of the original image 41 and the smoothed image 42.

The variation value is, for example, a standard deviation value, (the maximum value–the minimum value) and so forth. The variation value is a value indicating a variation of each small region and may be a statistic calculated from the pixel values of the pixels included in each small region. In the following, description will be made by giving the standard deviation value as an example in order to avoid confusion.

Here, for the convenience of explanation, serial numbers i=1, . . . I are allocated to the small regions and attention will be paid to an i-th small region. The standard deviation value of the original image 41 in the i-th small region is put as $\sigma_i^{(org)}$ and the standard deviation value of the smoothed image 42 is put as $\sigma_i^{(smt)}$.

<Step S204>

The arithmetic device 5 calculates a decreasing rate of the variation value of the smoothed image 42 based on the variation value of the original image 41 for every small region. In the present embodiment, the decreasing rate of the standard deviation value is calculated. For the i-th small region, the decreasing rate of the standard deviation value of the smoothed image 42 based on the standard deviation value of the original image 41 is put as $\rho_i$ and is calculated by the following formula.

[Numerical Formula 3]

$$\rho_i = \frac{\sigma_i^{(org)} - \sigma_i^{(smt)}}{\sigma_i^{(org)}} \tag{3}$$

The arithmetic device 5 calculates the decreasing rate $\rho_i$ of the standard deviation value in all of the small regions on the basis of the formula (3). The shape of the nonlinear function is determined using a feature amount (for example, the decreasing rate $\rho_i$) calculated from the pixel values of the pixels in both of the original image 41 and the smoothed image 42 as in the formula (3) and the processing illustrated in FIG. 4 is performed, thereby meeting the aforementioned "(Constraint Condition 3) The target image is to be suppressed in increase in noise such as the streak artifact and so forth in a region (=one of the flat regions) which is thought to be the same organ in comparison with the smoothed image".

Incidentally, in related art (for example, Japanese Patent No. 3700798 and Japanese Patent Application Laid-Open No. Hei07-93543) relating to the technique of mixing together two images which are the same as each other in original information, only the feature amount calculated from the pixel values of the pixels included in only one of the images is used. For example, with the standard deviation value calculated from the pixel values of the pixels included in only one of the images, it is difficult to discriminate between whether the noise has been reduced and whether the structure has blurred as a result of execution of an arbitrary smoothing process. Accordingly, it is difficult for related art to generate such a target image that the streak artifact is removed as generated in the embodiment of the present invention.

<Step S205>

The arithmetic device 5 extracts a feature amount calculation region from the set of small regions on the basis of the decreasing rate $\rho_i$.

In the first embodiment, the arithmetic device 5 extracts a small region whose decreasing rate has a maximum value in the small regions included within a predetermined range (for example, in the same slice) as the feature amount calculation region. Incidentally, the predetermined range may be either in a plurality of slices or in all of the slices.

In the following, description will be made assuming that a k-th small region has been extracted as the feature amount calculation region.

<Step S206>

The arithmetic device 5 determines the shape of the nonlinear function from the feature amount calculated from the pixel values of the pixels included in the feature amount calculation region (the k-th small region). In the following, an example that the feature amount is calculated by using a standard deviation value $\sigma_k^{(org)}$ of the original image 41 calculated in step S202 and a standard deviation value $\sigma_k^{(smt)}$ of the smoothed image 42 calculated in step S203 will be described. However, the present invention is not limited to this example and another variation value (for example, the difference between the maximum value and the minimum value of the pixels in the small region concerned) may be used in place of the standard deviation value.

An arbitrary constant is putt as $\alpha(0<\alpha<1)$ and the shape of the nonlinear function is set such that the condition coefficient takes the value of $\alpha$ when the difference in pixel value is $\sigma_k$ (a general notation of $\sigma_k^{(org)}$ and $\sigma_k^{(smt)}$ (see FIG. 3). $\alpha$ is an actual value such as, for example, 0.99, 0.98, 0.97 or the like. For example, for the generalized Gaussian function in the formula (1), the parameter $v$ for adjusting the bending position of the function is defined as in the following formula.

[Numerical Formula 4]

$$v^p = -\frac{(t\sigma_k)^p}{2\ln\alpha} \sum_{r \in N_s} w_{sr} \qquad (4)$$

Here, t is a positive coefficient which is not 1 and is empirically determined from statistical information obtained from already photographed images by taking the influence of the noise such as the streak artifact and so forth into account. For example, for an image that only Gaussian noise (the granular noise) is generated, t=1 is put and introduction of t into the formula (4) may be unnecessary. However, the embodiment of the present invention targets on the image that the streak artifact which is the noise stronger than the Gaussian noise is generated, t of a value larger than 1 is introduced into the formula (4).

In the formula (4), the parameters for adjusting the bending positions of the nonlinear functions calculated in the original image 41 and the smoothed image 42 respectively are put as $\sigma_k^{(org)}$ and $\sigma_k^{(smt)}$.

Figure 5:
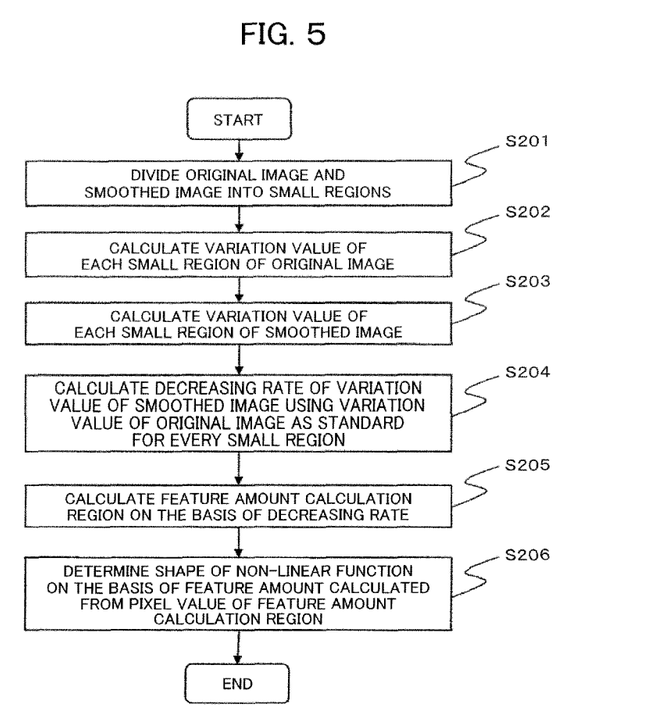
FIG. 5 is a diagram illustrating one example of a processing flow pertaining to the function shape determination step.

The arithmetic device 5 dynamically determines the shape of the nonlinear function for every predetermined range (for example, for every slice) by executing the processing illustrated in FIG. 5. One of the features of the first embodiment lies in the point that the region whose decreasing rate $\rho_i$ of the standard deviation value of the smoothed image 42 to the standard deviation value of the original image 41 has a maximum value is extracted as the feature amount calculation region and the shape of the nonlinear function is determined using the standard deviation value of the feature amount calculation region.

The aforementioned projection data smoothing filter has such a characteristic that it greatly decreases the streak artifact. Owing to this characteristic, the decreasing rate $\rho_i$ of the standard deviation value is increased in the small region including the streak artifact. In addition, the projection data smoothing filter also has such a characteristic that blurring of the structure is involved. Owing to this characteristic, since the standard deviation value of the original image is increased in the small region including the structure and the denominator in the formula (3) is increased, the decreasing rate $\rho_i$ of the standard deviation value is decreased consequently. That is, the possibility that the region whose the decreasing rate $\rho_i$ of the standard deviation value has the maximum value may include the streak artifact is high.

Therefore, extraction of the region whose decreasing rate $\rho_i$ of the standard deviation value has the maximum value as the feature amount calculation region leads to extraction of the small region which includes the streak artifact as the feature amount calculation region. Then, it is possible to obtain the target image that the streak artifact is removed eventually by substituting the standard deviation value of the small region which includes the streak artifact into the formula (4) and determining the value of the parameter $v$ for adjusting the bending position of the nonlinear function.

Getting back to the description of the flow in FIG. 4, in the following, processes of calculating the condition coefficients indicating the respective conditions of the original image 41 and the smoothed image 42 using the nonlinear function and calculating the weighting coefficient for weighted addition from the condition coefficients of the original image 41 and the smoothed image 42 will be described.

<Step S102>

The arithmetic device 5 calculates the condition coefficients of the original image 41 and the smoothed image 42 using the nonlinear function whose shape is determined in step S101. The process of calculating the condition coefficients is executed following the formula (1).

<Step S103>

The arithmetic device 5 calculates the weighing coefficient of each pixel of the original image 41 and the smoothed image 42 by using the condition coefficients calculated in step S102. The image vector of the original image 41 is put as $x^{(org)}=\{x_1^{(org)}, \ldots, x_J^{(org)}\}$ and the image vector of the smoothed image 42 is put as $x^{(smt)}=\{x_1^{(smt)}, \ldots, x_J^{(smt)}\}$. In weighted addition of the images, the weighting coefficient pertaining to the pixel of interest s is put as $\lambda_s$. The process of calculating $\lambda_s$ is executed following any one of the following formula (5), formula (6) and formula (7).

[Numerical Formula 5]

$$\lambda_s = g_s(x^{(org)}, v_k^{(org)}) \cdot g_s(x^{(smt)}, v_k^{(smt)}) \qquad (5)$$

[Numerical Formula 6]

$$\lambda_s = \{g_s(x^{(org)}, v_k^{(org)}) + g_s(x^{(smt)}, v_k^{(smt)})\}/2 \qquad (6)$$

[Numerical Formula 7]

$$\lambda_s = \{g_s(x^{(org)}, v_k^{(org)}) \cdot g_s(x^{(smt)}, v_k^{(smt)})\}^{1/2} \qquad (7)$$

One of the features of the embodiment of the present invention lies in the point that the values of the weighting coefficients of the mutually corresponding pixels are calculated using the condition coefficients of both of the original image 41 and the smoothed image 42 as expressed in the formula (5) to the formula (7).

In the formula (5) and the formula (7), in a case where the condition coefficient takes a value close to 1 in at least either of the original image 41 and the smoothed image 42 and it is decided that the pixel of interest s corresponds to an edge part of the structure, the weighting coefficient takes a value close to 0. On the other hand, in a case where the condition coefficients of both of the original image 41 and the smoothed image 42 take values close to 1 and it is decided that the pixel of interest s corresponds to a flat region (for example, a region which is thought to be the same organ), the weighting coefficient takes a value close to 1.

In the formula (6), in a case where the condition coefficients of both of the original image 41 and the smoothed image 42 take values close to 0, the weighting coefficient takes a value close to 0. In addition, in the formula (6), in a case where the condition coefficients of both of the original image 41 and the smoothed image 42 tales values close to 1, the weighting coefficient takes a value close to 1. On the other hand, in the formula (6), in a case where a difference in value of condition coefficient between the original image 41 and the smoothed image 42 is large, a mean value of the both is defined as the weighting coefficient.

Considering from the above, in a case where it is desired to sharply recover the edge of the structure in the target image, it is desirable to use the formula (5) or the formula (7). On the other hand, in a case where it is desired to smoothly recover the edge of the structure in the target image, it is desirable to use the formula (6). The both ways of recovering the edge may be properly used depending on the application.

<Step S104>

The arithmetic device 5 generates the target image by performing weighed addition of the original image 41 and the smoothed image 42 by using the weighting coefficient calculated in step S103. The image vector of the target image after weighted addition has been performed is set as $x^{(mrg)}=\{x_1^{(mrg)}, \ldots, x_J^{(mrg)}\}$. The arithmetic device 5 performs weighted addition for the pixel of interest s of the target image by using the following formula.

[Numerical Formula 8]

$$x_s^{(mrg)} = \lambda_s (x_s^{(smt)} - x_s^{(org)}) + x_s^{(org)} \quad (8)$$

The aforementioned "(Constraint Condition 1) The pixel value of the target image is to be within a range of pixel values of mutually corresponding pixels in the original image and the smoothed image" is met by performing weighted addition by using the formula (8).

Figure 7:
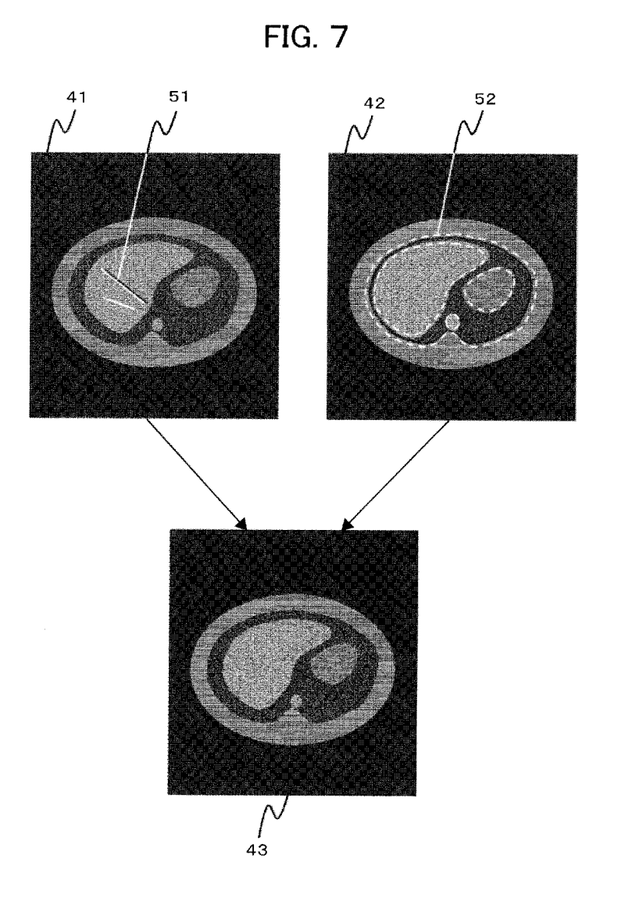
FIG. 7 is a diagram illustrating examples of the original image, the smoothed image and the target image.

Examples of schematic diagrams of the original image 41, the smoothed image 42 and a target image 43 are illustrated in FIG. 7. As illustrated in FIG. 7, a streak artifact 51 is being generated in the original image 41.

In addition, a blur 52 of the edge of the structure is being generated in the smoothed image 42. It is possible to generate the target image 43 that the edge of the structure is maintained and the streak artifact 51 is removed from such original image 41 and smoothed image 42 as mentioned above by the image processing method according to the embodiment of the present invention illustrated in FIG. 4. As illustrated in FIG. 7, the edge of the structure is maintained and the streak artifact 51 is removed in the target image 43.

[Second Embodiment]

In the following, the second embodiment of the present invention will be described. Incidentally, description of the contents which are common to the first embodiment is omitted.

In the first embodiment, the small region whose decreasing rate of the variation value of the smoothed image 42 to the variation value of the original image 41 has the maximum value is extracted as the feature amount calculation region and the parameter ν for adjusting the bending position of the nonlinear function is determined on the basis of the feature amount of the feature amount calculation region. At that time, the feature amount calculation region is extracted by analyzing in more detail the relation between the decreasing rate of the variation value and the variation value of the original image 41 or the smoothed image 42. Owing to this, the precision that the flat region including the streak artifact 51 is extracted as the feature amount calculation region is improved.

In the second embodiment, the arithmetic device 5 extracts m higher-rank small regions which are higher in decreasing rate $\rho_i$ of the standard deviation value in the small regions included within the predetermined range (for example, in the same slice) in step S205 in FIG. 5. That is, the arithmetic device 5 extracts the small regions counted from the small region whose decreasing rate $\rho_i$ of the standard deviation value has the maximum value down to an m-th ranked small region. Here, m is an arbitrary constant and is empirically determined.

Next, the arithmetic device 5 extracts the small region whose standard deviation value has a maximum value in m higher-rank small regions as the feature amount calculation region in each of the original image 41 and the smoothed image 42. The feature amount calculation process, the nonlinear function shape determination process, the condition coefficient calculation process, the weighing coefficient calculation process, the weighted addition process and so forth which are succeeding processes are the same as those in the first embodiment.

According to the second embodiment, the precision that the flat region including the streak artifact 51 is extracted as the feature amount calculation region is improved.

It is apparent that the object of the present invention is attained from the above-mentioned description relating to the various embodiments of the present invention. Although the present invention has been described and illustrated in detail, they simply aim at description and illustration and the present invention is not limited to them. In addition, the gist of the present invention is to be limited only by the scope of the patent claims.

DESCRIPTION OF REFERENCE NUMERALS OR SYMBOLS

1: X-ray CT apparatus, 2: scanner, 3: operation unit, 4: bed, 5: arithmetic device, 6: input device, 7: display device, 8: memory device, 10: test object, 11: X-ray tube, 41: original image, 42: smoothed image, 43: target image, 51: streak artifact, 52: blur of structure edge

What is claimed is:

1. An image processing device for adding respective mutually corresponding pixels of an original image, including streak artifact, generated from original information and of a smoothed image generated from the same original information and reduced at least in the streak artifact with weighting using a weighting coefficient and generating a target image that an edge of a structure is maintained and the streak artifact is removed, comprising:
    a function shape determination unit that determines a shape of a nonlinear function on the basis of feature amounts of the original image and the smoothed image; and
    a weighting coefficient calculation unit that calculates the weighing coefficient on the basis of the nonlinear function,
    wherein the function shape determination unit includes
        a division unit that divides regions of the original image and the smoothed image into plural mutually corresponding small regions,
        a decreasing rate calculation unit that calculates variation values for the small regions pertaining to both of the original image and the smooth image and calculates a decreasing rate of the variation value of the smoothed image based on the variation value of the original image, for each of the small regions, a region extraction unit that extracts a feature amount calculation region from a set of the small regions on the basis of the decreasing rate, and a feature amount calculation unit that calculates the feature amount from a pixel value of the feature amount calculation region.

2. The image processing device according to claim 1, wherein the region extraction unit extracts the small region the decreasing rate of which is maximum within a predetermined range as the feature amount calculation region.

3. The image processing device according to claim 1, wherein the region extraction unit extracts the small region the variation value of which is maximum in the small regions counted from the small region the decreasing rate of which is maximum down to the small region ranked to a fixed order within a predetermined range as the feature amount calculation region.

4. The image processing device according to claim 1, wherein the nonlinear function is a smooth and continuous function that a difference in pixel value between a pixel of interest of the original image or the smoothed image and a pixel adjacent to the pixel of interest is set as a variable.

5. The image processing device according to claim 4, wherein the nonlinear function is a function which approaches 1 as the difference in pixel value is decreased and approaches 0 as the difference in pixel value is increased.

6. The image processing device according to claim 1, wherein the weighting coefficient calculation unit calculates condition coefficients indicating respective conditions of the original image and the smoothed image by using the nonlinear function and calculates the weighting coefficient on the basis of the condition coefficients.

7. An image processing method of adding respective mutually corresponding pixels of an original image generated from original information and of a smoothed image generated from the same original information and reduced at least in streak artifact with weighting using a weighting coefficient and generating a target image that an edge of a structure is maintained and the streak artifact is removed, comprising:

the function shape determination step of determining a shape of a nonlinear function on the basis of feature amounts of the original image and the smoothed image; and the weighting coefficient calculation step of calculating the weighting coefficient on the basis of the nonlinear function, wherein the function shape determination step includes a division step of dividing regions of the original image and the smoothed image into plural mutually corresponding small regions, a decreasing rate calculation step of calculating variation values for the small regions pertaining to both of the original image and the smooth image and calculating a decreasing rate of the variation value of the smoothed image based on the variation value of the original image, for each of the small regions, a region extraction step of extracting a feature amount calculation region from a set of the small regions on the basis of the decreasing rate, and a feature amount calculation step of calculating the feature amount from a pixel value of the feature amount calculation region.

8. The image processing method according to claim 7, wherein the region extraction step is adapted to extract the small region the decreasing rate of which is maximum within a predetermined range as the feature amount calculation region.

9. The image processing method according to claim 7, wherein the region extraction step is adapted to extract the small region the variation value of which is maximum within the small regions counted from the small region the decreasing rate of which is maximum down to the small region ranked to a fixed order within a predetermined range as the feature amount calculation region.

10. The image processing method according to claim 7, wherein the nonlinear function is a smooth and continuous function that a difference in pixel value between a pixel of interest of the original image or the smoothed image and a pixel adjacent to the pixel of interest is set as a variable.

11. The image processing method according to claim 10, wherein the nonlinear function is a function which approaches 1 as the difference in pixel value is decreased and approaches 0 as the difference in pixel value is increased.

12. The image processing method according to claim 7, wherein the weighting coefficient calculation step is adapted to calculate condition coefficients indicating respective conditions of the original image and the smoothed image by using the nonlinear function and calculate the weighting coefficient on the basis of the condition coefficients.

13. The image processing method according to claim 7, wherein the nonlinear function is defined by a condition coefficient $g_s(x)$ of a pixel of interest s, calculated based on the following formula (1), in which $x = \{x1, \ldots, xj\}$ is an image vector, $N_s$ is a set of adjacent pixels r relative to the pixel of interest s, p is an arbitrary parameter for adjusting the gradient of the generalized Gaussian function, v is an arbitrary parameter for adjusting a bending position of the generalized Gaussian function, $W_{sr}$ is a weighting coefficient according to a distance between the pixel of interest s and the adjacent pixel r, and wherein the shape of the nonlinear function is determined by the value of v $$g_s(x, v) \equiv \exp\left\{-\sum_{r \in N_s} \frac{w_{sr}|x_s - x_r|^p}{2v^p}\right\}. \quad (1)$$

14. The image processing device according to claim 1, wherein the nonlinear function is defined by a condition coefficient $g_s(x)$ of a pixel of interest s, calculated based on the following formula (1), in which $x = \{x1, \ldots, xj\}$ is an image vector, $N_s$ is a set of adjacent pixels r relative to the pixel of interest s, p is an arbitrary parameter for adjusting the gradient of the generalized Gaussian function, v is an arbitrary parameter for adjusting a bending position of the generalized Gaussian function, $W_{sr}$ is a weighting coefficient according to a distance between the pixel of interest s and the adjacent pixel r, and wherein the shape of the nonlinear function is determined by the value of $v$ $$g_s(x, v) \equiv \exp\left\{-\sum_{r \in N_s} \frac{w_{sr}|x_s - x_r|^p}{2v^p}\right\}. \tag{1}$$

* * * * *

UNITED STATES PATENT AND TRADEMARK OFFICE
CERTIFICATE OF CORRECTION

PATENT NO. : 9,454,804 B2  
APPLICATION NO. : 14/372330  
DATED : September 27, 2016  
INVENTOR(S) : Hisashi Takahashi, Koichi Hirokawa and Taiga Goto Page 1 of 1

It is certified that error appears in the above-identified patent and that said Letters Patent is hereby corrected as shown below:

On the Title Page

Add the following Item (30) [Foreign Application Priority Data]

--(30) Foreign Application Priority Data:  
Mar. 27, 2012 [JP] ........................ 2012-070823.--

Signed and Sealed this  
Second Day of May, 2017

Michelle K. Lee  
*Director of the United States Patent and Trademark Office*